United States Patent [19]
Robin et al.

[11] Patent Number: 5,643,885
[45] Date of Patent: Jul. 1, 1997

[54] ETOPOSIDE DERIVATIVES, PROCESS FOR PREPARING THEM, THEIR USE AS A MEDICINAL PRODUCT AND THEIR USE FOR THE PREPARATION OF A MEDICINAL PRODUCT INTENDED FOR ANTI-CANCER TREATMENT

[75] Inventors: Jean-Pierre Robin, Le Mans, France; Robert Kiss, Brussels, Belgium; Thierry Imbert, Viviers-les-Montagnes, France

[73] Assignee: Pierre Fabre Medicament, Boulogne, France

[21] Appl. No.: 464,646
[22] PCT Filed: Dec. 20, 1993
[86] PCT No.: PCT/FR93/01270
§ 371 Date: Jun. 21, 1995
§ 102(e) Date: Jun. 21, 1995
[87] PCT Pub. No.: WO94/14829
PCT Pub. Date: Jul. 7, 1994

[30] Foreign Application Priority Data

Dec. 22, 1992 [FR] France .................. 92 15460

[51] Int. Cl.$^6$ .................. A61K 31/70; C07H 15/26
[52] U.S. Cl. .................. 514/27; 514/25; 536/17.1; 536/18.1; 536/18.2
[58] Field of Search .................. 536/18.1, 18.2, 536/17.1; 514/25, 27

[56] References Cited

U.S. PATENT DOCUMENTS 5,206,350  4/1993  Wang et al. .................. 536/18.1

*Primary Examiner*—Elli Peselev
*Attorney, Agent, or Firm*—The Firm of Gordon W. Hueschen

[57] ABSTRACT

Compound of the formula (I) in which R' is a hydrogen atom or a radical R and R is an acyl residue. The invention also concerns the use of said compounds in the treatment of cancer and pharmaceutical compositions comprising said compounds.

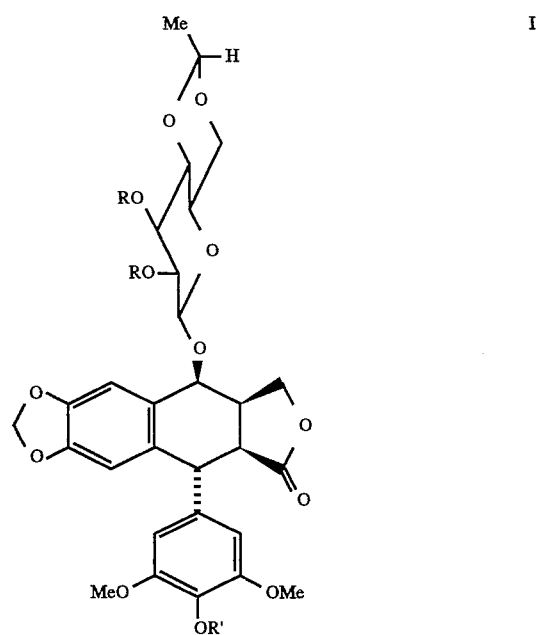

14 Claims, No Drawings

ETOPOSIDE DERIVATIVES, PROCESS FOR PREPARING THEM, THEIR USE AS A MEDICINAL PRODUCT AND THEIR USE FOR THE PREPARATION OF A MEDICINAL PRODUCT INTENDED FOR ANTI-CANCER TREATMENT

The present invention relates to etoposide derivatives, to a process for preparing them and to their use as an anticancer medicinal product.

Etoposide a and some of its derivatives such as teniposide b

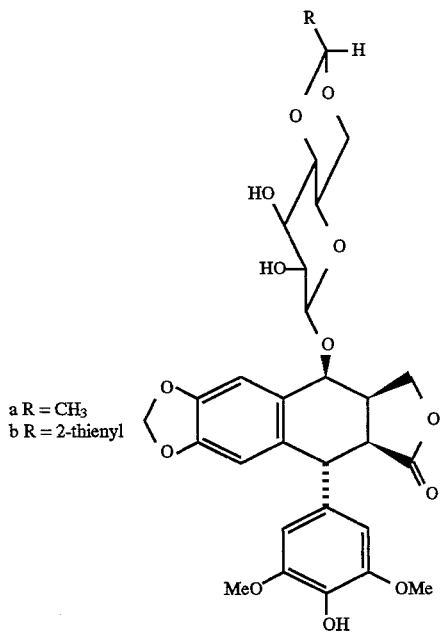

a R = CH₃
b R = 2-thienyl are known to have antitumor activities which are useful in human clinical medicine. They are derived, on the one hand from a natural stock, especially from podophyllotoxin

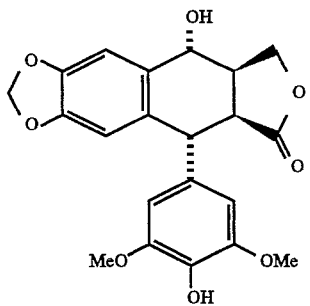

and on the other hand from a glycosylated portion, especially a 4,6-ethylidene-β-D-glucopyranose.

The synthesis of etoposide has been described in U.S. Pat. No. 3,524,844. It has also been the subject of many publications (J. Med. Chem. (1971), 14, 936; J. Org. Chem. (1981), 46, 2826 and more recently: Heterocycles (1991), 32, 859; Tetrahedron (1991), 47, 4675; Synthesis (1991), 275).

Etoposide and its analog teniposide are commercially available as medicinal products for the treatment of a number of cancerous tumors, as well as in acute leukemias in relapse.

The major drawback of these medicinal products lies in the fact that they give rise to a large number of undesirable side effects, such as leukopenia or thrombocytopenia.

A large number of etoposide derivatives have been proposed in the literature, in particular in Patent Applications EP-A-0,401,800, EP-A-0,461,556, EP-A-0,455,159, EP-A-0,433,678, EP-A-0,358,197, EP-A-0,415,453, EP-A-0,320,988, EP-A-0,423,747, EP-A-0,394,907 or EP-A-0,445,021.

Some of these derivatives are, in particular, described as intermediate products in the synthesis of etoposide.

In point of fact, it was found, unexpectedly, that some etoposide derivatives displayed improved anticancer activity while showing lower toxicity, enabling these products to be administered on a chronic basis as medicinal products.

The present invention hence relates to a compound of general formula I:

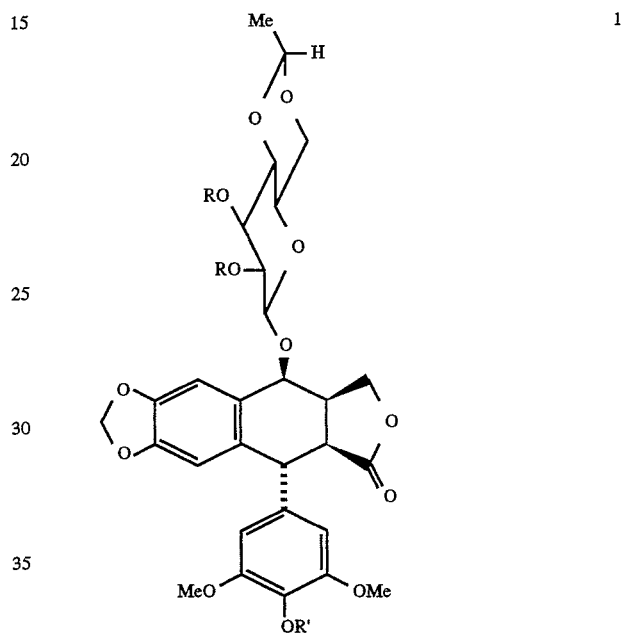

in which

R' represents a hydrogen atom or a radical R, and

R represents a group of formula

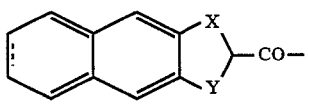

or an acyl residue of formula

in which formulae

X, Y and Z independently represent an oxygen atom or a sulfur atom, and

A represents
a linear or branched $C_1$–$C_4$ alkyl radical,
a $C_3$–$C_6$ cycloalkyl radical,
an aryl radical chosen especially from phenyl, phenyl (linear or branched $C_1$–$C_4$ alkyl ) and naphthyl radicals and these same radicals substituted with one to three substituents chosen from hydroxyl radicals, linear or branched $C_1$–$C_4$ alkoxy radicals optionally perhalogenated with chlorine or fluorine atoms, benzyloxy, phenyl and linear or branched $C_1$–$C_4$ alkyl radicals and halogen atoms, especially chlorine or fluorine, and its physiologically acceptable salts,
on the condition that, when R' represents a radical R, R is chosen from 4-fluorophenoxyacetyl, 4-benzyloxyphenoxyacetyl, 4-hydroxyphenoxyacetyl, 4-methylphenoxyacetyl, 3,4,5-trimethoxyphenoxyacetyl, 3,4-methylenedioxyphenoxyacetyl, 2,3-dimethoxyphenoxyacetyl, 4-(trifluoromethoxy) phenoxyacetyl, 4-phenylphenoxyacetyl, 2-naphthoxyacetyl, 1-naphthoxyacetyl, cyclohexylacetyl, 4-methylphenoxyacetyl and 3,4-dimethoxyphenoxyacetyl radicals.

Linear or branched $C_1$–$C_4$ alkyl will preferably be understood to mean methyl, ethyl, propyl and butyl radicals, these same definitions applying to the alkyl residues of the phenyl alkyl and alkoxy radicals.

Advantageously, the compounds of general formula I will be chosen with R' representing a hydrogen atom.

For its part, R will preferably be chosen from ethoxyacetyl, phenoxyacetyl, 4-methoxyphenoxyacetyl, 2-methoxyphenoxyacetyl, 4-nitrophenoxyacetyl, 2-nitrophenoxyacetyl, 2,4-dichlorophenoxyacetyl, 2,4,5-trichlorophenoxyacetyl, 2,4,6-trichlorophenoxyacetyl, 4-fluorophenoxyacetyl, 2-fluorophenoxyacetyl, 4-hydroxyphenoxyacetyl, 4-benzyloxyphenoxyacetyl, 4-methylphenoxyacetyl, 3,4,5-trimethoxyphenoxyacetyl, 3,4-methylenedioxyphenoxyacetyl, 2,3-dimethoxyphenoxyacetyl, 4-(trifluoromethoxyphenoxyacetyl, 4-phenylphenoxyacetyl, 2-naphthoxyacetyl, 1-naphthoxyacetyl, cyclohexylacetyl, 4-methylphenoxyacetyl and 3,4-dimethoxyphenoxyacetyl radicals.

The present invention also relates to a process for preparing a compound of general formula I, for which a glycosyl intermediate of general formula 2

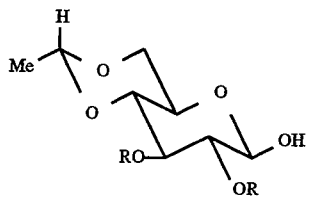

2 is reacted with an intermediate of formula 3

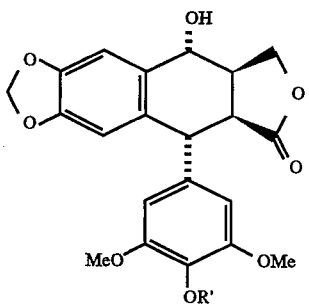

3 for which formulae R and R' are defined above, and the phenol functions of the compound of formula I obtained are, where appropriate, deprotected.

The general scheme of synthesis of the compounds according to the invention and of the intermediates of formulae 2 and 3 is shown below, for R representing a phenoxyacetyl radical and R' representing a hydrogen atom or a benzyloxycarbonyl radical.

Naturally, the synthesis of all of the compounds of formula I may be modeled on the one presented in this scheme.

To interpret this schemes, phenoxyacetyl radical will be understood generically to mean all the radicals R defined above. Z will also be employed to denote the benzyloxycarbonyl radical.

The synthesis process used consists in preparing 4,6-ethylidene-β-D-glucose protected on its anomeric hydroxyl by a benzyloxycarbonyl (Z), and then esterifying the 2 alcohol functions at positions 2 and 3 with phenoxyacetyl residues to yield protected glycosyl intermediates, which are then deprotected by catalytic hydrogenation in the presence of Pd/C in a conventional manner.

The preparation of these derivatives is, moreover, described in Patent Application EP-A-0,445,021.

These intermediates are then condensed with a 4'-demethylepipodophyllotoxin derivative protected on the phenol at position 4' by Z, the preparation of which is, in particular, described in Patent Application EP-A-0,401,800. The condensation is performed at low temperature in the vicinity of −20° C. in the presence of a Lewis acid such as, for example, $BF_3$ etherate in a chlorinated hydrocarbon, especially methylene chloride, to yield the derivatives of general formula I for which R' represents a benzyloxycarbonyl radical.

[FIN: CHANGES TO FOLLOWING REACTION SCHEME:

top left: 4'-demethyl-4'OZ please put a hyphen after the OZ and remove final e from epipodophyllotoxine at right: above vertical arrow should read 4'-demethylepipodophyllotoxin then underneath the arrow:

4'-demethyl-4'-phenoxyacetyl(epipodophyllotoxin)

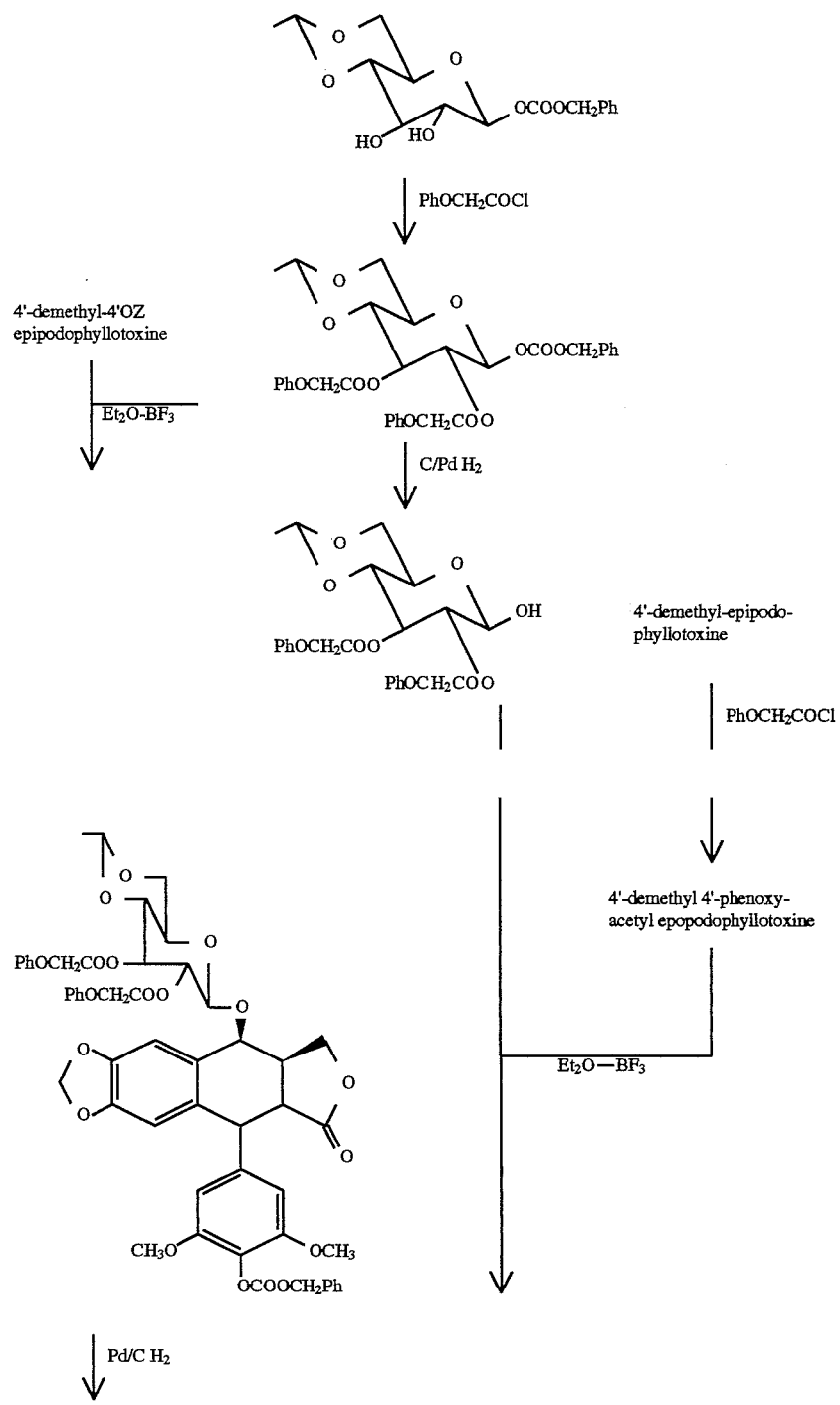

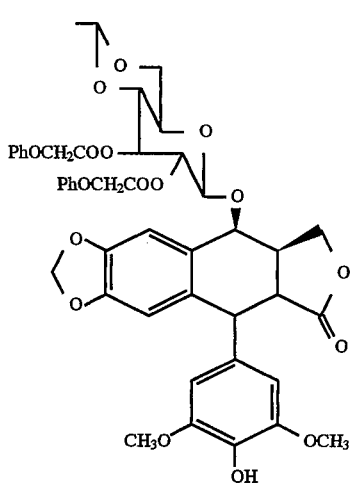 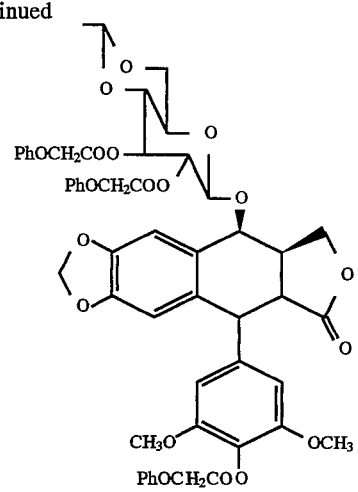

-continued

The presence of an anomeric hydroxyl function on the glycosyl intermediate always gives rise to the problem of the stereochemistry of the product obtained, and of controlling it.

By the process according to the present invention, a minimal fraction of undesirable α anomer is obtained, enabling the compound according to the invention to be obtained directly without necessitating a subsequent purification.

The final stage yielding the compound according to the invention for which R' represents a hydrogen atom is carried out in a conventional manner by catalytic hydrogenation in the presence of Pd/C at room temperature.

The examples below of compounds of general formula I enable the present invention to be illustrated without, however, seeking to limit its scope.

EXAMPLE 1

Synthesis of 4'-phenoxyacetyl-4'-demethyl-4-O-[2, 3-bis(phenoxyacetyl)-4,6-ethylideneglucosyl] epipodophyllotoxin 4'-(2-phenoxyacetyl)-4'-demethylepipodophyllotoxin (3 kg, equivalent to 5.62 mol) and 2,3-bis(2-phenoxyacetyl)-4,6-ethylidene-β-D-glucose (3.2 kg, equivalent to 6.74 mol or 1.2 eq.) were introduced into dry dichloromethane (18 liters). When the temperature was stabilized at −18° C., boron trifluoride etherate (1.73 l, equivalent to 14.05 mol, equivalent to 2.5 eq.) was added slowly. Reaction was continued at —18° C. for 2 h and then, after monitoring by thin-layer chromatography, pyridine (910 ml, equivalent to 2 eq.) was added. The solution was washed with water, then dried over $MgSO_4$ and concentrated under reduced pressure. The crude product was filtered through silica gel (70–200μ; MeOH (2%)/$CH_2Cl_2$) and, after evaporation, 4.73 kg of an amorphous white powder were obtained. A sample was crystallized for the purpose of an analytical study. The results are as follows:

Empirical formula: $C_{53}H_{50}O_{19}$ Molar mass: 990 Yield: 85% M.p.: 132°–134° C. $[\alpha°]^{22}D=-67°$ (c=1; $CHCl_3$)

EXAMPLE 2

4'-(2-methoxyphenoxyacetyl)-4'-demethyl-4-O-[2,3-bis(2-methoxyphenoxyacetyl)-4,6-ethylideneglucosyl]epipodophyllotoxin The procedure of Example 1 was repeated, but using 2,3-bis[2-(2-methoxyphenoxy)acetyl)]-4,6-ethylidene-β-D-glucose and 4'-[2-(2-methoxyphenoxy)acetyl)]-4'-demethylepipodophyllotoxin, respectively, in place of 2,3-(2-phenoxyacetyl)-4,6-ethylidene-β-D-glucose and 4'-(2-phenoxyacetyl)-4'-demethylepipodophyllotoxin, to obtain the desired product.

Empirical formula: $C_{56}H_{56}O_{22}$ Molar mass: 1080 Yield: 75% M.p.: 113°–115° C. $[\alpha°]^{22}D=-52°$ (c=1; $CHCl_3$)

EXAMPLE 3

4'-(4-methoxyphenoxyacetyl)-4'-demethyl-4-O-[2,3-bis(4-methoxyphenoxyacetyl)-4,6-ethylideneglucosyl]epipodophyllotoxin The procedure of Example 1 was repeated, but using 2,3-bis[2-(4-methoxyphenoxy)acetyl)]-4,6-ethylidene-β-D-glucose and 4'-[2-(4-methoxyphenoxy)acetyl)]-4'-demethylepipodophyllotoxin, respectively, in place of 2,3-(2-phenoxyacetyl)-4,6-ethylidene-β-D-glucose and 4'-(2-phenoxyacetyl)-4'-demethylepipodophyllotoxin, to obtain the desired product.

Empirical formula: $C_{56}H_{56}O_{22}$ Molar mass: 1080 Yield: 73% M.p.: 107°–109° C. $[\alpha°]^{22}D=-61°$ (c=1; $CHCl_3$)

EXAMPLE 4

4'-(2-nitrophenoxyacetyl)-4'-demethyl-4-O-[2,3-bis (2-nitrophenoxyacetyl)-4,6-ethylideneglucosyl] epipodophyllotoxin The procedure of Example 1 was repeated, but using 2,3-bis[2-(2-nitrophenoxy)acetyl)]-4,6-ethylidene-β-D-glucose and [2-(2-nitrophenoxy)acetyl)]-{4'4'-demethylepipodophyllotoxin}, respectively, in place of 2,3-(2-phenoxyacetyl)-4,6-ethylidene-β-D-glucose and 4'-(2-phenoxyacetyl)-4'-demethylepipodophyllotoxin, to obtain the desired product.

Empirical formula: $C_{53}H_{47}O_{25}N_3$ Molar mass: 1125 Yield: 79% M.p.: 135°–137° C.

EXAMPLE 5

4'-(4-nitrophenoxyacetyl)-4'-demethyl-4-O-[2,3-bis (4-nitrophenoxyacetyl)-4,6-ethylideneglucosyl] epipodophyllotoxin The procedure of Example 1 was repeated, but using 2,3-bis[2-(4-nitrophenoxy)acetyl)]-4,6-ethylidene-β-D- glucose and 4'-[2-(4-nitrophenoxy)acetyl)]-4'-demethylepipodophyllotoxin, respectively, in place of 2,3-(2-phenoxyacetyl)-4,6-ethylidene-β-D-glucose and 4'-(2-phenoxyacetyl)-4'-demethylepipodophyllotoxin, to obtain the desired product.

Empirical formula: $C_{53}H_{47}O_{25}N_3$ Molar mass: 1125 Yield: 82% M.p.: 143°–145° C. $[\alpha°]^{22}D=-72°$ (c=1; CHCl$_3$)

EXAMPLE 6

4'-(2,4-dichlorophenoxyacetyl)-4'-demethyl-4-O-[2,3-bis(2,4-dichlorophenoxyacetyl)-4,6-ethylideneglucosyl]epipodophyllotoxin The procedure of Example 1 was repeated, but using 2,3-bis[2-(2,4-dichlorophenoxy)acetyl)]-4,6-ethylidene-β-D-glucose and 4'-[2-(2,4-dichlorophenoxy)acetyl)]-4'-demethylepipodophyllotoxin, respectively, in place of 2,3-(2-phenoxyacetyl)-4,6-ethylidene-β-D-glucose and 4'-(2-phenoxyacetyl)-4'-demethylepipodophyllotoxin, to obtain the desired product.

Empirical formula: $C_{53}H_{44}O_{19}Cl_6$ Molar mass: 1197 Yield: 85% M.p.: 115°–117° C. $[\alpha°]^{22}D=-51°$ (c=1; CHCl$_3$)

EXAMPLE 7

4'-(2,4,5-trichlorophenoxyacetyl)-4'-demethyl-4-O-[2,3-bis(2,4,5-trichlorophenoxyacetyl)-4,6-ethylideneglucosyl]epipodophyllotoxin The procedure of Example 1 was repeated, but using 2,3-bis[2-(2,4,5-trichlorophenoxyacetyl)]-4,6-ethylidene-β-D-glucose and 4'-[2-(2,4,5-trichlorophenoxy)acetyl)]-4'-demethylepipodophyllotoxin, respectively, in place of 2,3-(2-phenoxyacetyl)-4,6-ethylidene -β-D-glucose and 4'-(2-phenoxyacethyl)-4'-demethylepipodophyllotoxin, to obtain the desired product.

Empirical formula: $C_{53}H_{41}O_{19}Cl_9$ Molar mass: 1300.5 Yield: 75% M.p.: 126°–128° C. $[\alpha°]^{22}D=-43$ (c=1; CHCl$_3$)

EXAMPLE 8

4'-(2,4,6-trichlorophenoxyacetyl)-4'-demethyl-4-O-[2,3-bis(2,4,6-trichlorophenoxyacetyl)-4,6-ethylideneglucosyl]epipodophyllotoxin The procedure of Example 1 was repeated, but using 2,3-bis[2-(2,4,6-trichlorophenoxyacetyl)-4,6-ethylidene-β-D-glucose and 4'-[2-(2,4,6-trichlorophenoxy)acetyl)]-4'-demethylepipodophyllotoxin, respectively, in place of 2,3-(2-phenoxyacetyl)-4,6-ethylidene -β-D-glucose and 4'-(2-phenoxyacetyl)-4'-demethylepipodophyllotoxin, to obtain the desired product.

Empirical formula: $C_{53}H_{41}O_{19}Cl_9$ Molar mass: 1300.5 Yield: 80% M.p.: 120°–122° C. $[\alpha°]^{22}D=-10°$ (c=1; CHCl$_3$)

EXAMPLE 9

4'-(2-fluorophenoxyacetyl)-4'-demethyl-4-O-[2,3-bis(2-fluorophenoxyacetyl)-4-ethylideneglucosyl]epipodophyllotoxin The procedure of Example 1 was repeated, but using 2,3-bis[2-(2-fluorophenoxyacetyl)]-4,6-ethylidene -β-D-glucose and 4'-[2-(2-fluorophenoxy)acetyl)]-4'-demethylepipodophyllotoxin, respectively, in place of 2,3-(2-phenoxyacetyl)-4,6-ethylidene-β-D-glucose and 4'-(2-phenoxyacetyl)-4'-demethylepipodophyllotoxin, to obtain the desired product.

Empirical formula: $C_{53}H_{47}O_{19}F_3$ Molar mass: 1140 Yield: 57% M.p.: amorphous $[\alpha°]^{22}D=-58°$ (c=1; CHCl$_3$)

EXAMPLE 10

4'-ethoxyacetyl-4'-demethyl-4-O-[2,3-bis(ethoxyacetyl)-4,6-ethylideneglucosyl]epipodophyllotoxin The procedure of Example 1 was repeated, but using 2,3-bis[2-ethoxyacetyl)-4,6-ethylidene-β-D-glucose and 4'-(2-ethoxyacetyl)-4'-demethylepipodophyllotoxin, respectively, in place of 2,3-(2-phenoxyacetyl)-4'-ethylidene-β-D-glucose and 4'-(2-phenoxyacetyl) epipodophyllotoxin, to obtain the desired product.

Empirical formula: $C_{41}H_{50}O_{19}$ Molar mass: 846 Yield: 71% M.p.: 195°–198° C. $[\alpha°]^{22}D=-64°$ (c=1; CHCl$_3$)

EXAMPLE 11

4'-[2,2-(2,3-naphthylidenedioxy)acetyl]-4'-demethyl-4-O-[2,3-bis[2,2-(2,3-naphthylidenedioxy)acetyl]-4,6-ethylideneglucosyl]epipodophyllotoxin The procedure of Example 1 was repeated, but using 2,3-bis(2,2-naphthylidenedioxyacetyl)-4,-ethylidene-β-D-glucose and 4'-(2,2-naphthylidenedioxyacetyl) epipodophyllotoxin, respectively, in place of 2,3-(2-phenoxyacetyl)-4,6-ethylidene-β-D-glucose and 4'-(2-phenoxyacetyl)-4'-demethylepipodophyllotoxin, to obtain the desired product.

Empirical formula: $C_{65}H_{50}O_{22}$ Molar mass: 1182 Yield: 64% M.p.: 157°–159° C. $[\alpha]^{22}D=-40°$ (c=1; CHCl$_3$)

EXAMPLE 12

4'-benzylthioacetyl-4'-demethyl-4-O-[2,3-bis(benzylthioacetyl)-4,6-ethylideneglucosyl]epipodophyllotoxin The procedure of Example 1 was repeated, but using 2,3-bis(2-benzylthioacetyl)-4,6-ethylidene-β-D-glucose and 4'-(2-benzylthioacetyl)-4'-demethylepipodophyllotoxin, respectively, in place of 2,3-(2-phenoxyacetyl)-4,6-ethylidene-β-D-glucose and 4'-(2-phenoxyacetyl)-4'-demethylepipodophyllotixin, to obtain the desired product.

Empirical formula: $C_{56}H_{56}O_{16}S_3$ Molar mass: 1080 Yield: 49% M.p.: amorphous $[\alpha°]^{22}D=-48°$ (c=1; CHCl$_3$)

EXAMPLE 13

4'-phenylthioacetyl-4'-demethyl-4-O-[2,3-bis(phenylthioacetyl)-4,6-ethylideneglucosyl]epipodophyllotoxin The procedure of Example 1 was repeated, but using 2,3-bis(2-phenylthioacetyl)-4,6-ethylidene-β-D-glucose and 4'-(2-phenylthioacetyl)-4-demethylepipodophyllotoxin, respectively, in place of 2,3-(2-phenoxyacetyl)-4'-ethylidene-β-D-glucose and 4'-(2-phenoxyacetyl)-4'-demethylepipodophyllotoxin, to obtain the desired product.

Empirical formula: $C_{53}H_{50}O_{16}S_3$ Molar mass: 1038 Yield: 82% M.p.: amorphous $[\alpha°]^{22}D=-60°$ (c=1; CHCl$_3$)

EXAMPLE 14

4'-(4-fluorophenoxyacetyl)-4'-demethyl-4-O-[2,3-bis(4-fluorophenoxyacetyl)-4'-ethylideneglucosyl]epipodophyllotoxin The procedure of Example 1 was repeated, but using 2,3-bis(4-fluorophenoxyacetyl)]-4'-ethylidene-β-D-glucose and 4'-(4-fluorophenoxy)acetyl)-4'-demethylepipodophyllotoxin, to obtain the desired product, isolated by chromatography on a silica column (elution $CH_2Cl_3/MeOH$ 99:1) as an amorphous powder.

IR (Nujol, $\nu(cm^{-1})$): 1755, 1590, 1480, 1150, 1080, 820, 720.

$^1$H NMR (400 MHz, $CDCl_3$) δ, ppm: 6.9 (m,8H,Ar); 6.79 (m,2H,Ar); 6.77 (s,1H,H-5); 6.67 (m,2H,Ar); 6.51 (s,1H-8); 6.26 (s,2H,H-2',H-6); 5.92 (d,1H,J=1.0Hz,OCHAO); 5.71 (d,1H,J=0.9Hz,OCHBO); 5.34 (t,1H,J3-2=9.4Hz,H-3"); 5.03 (dd,1H,J2-1=7.9Hz,J2-3=9.2Hz, H-2"); 4.91 (d,1H,J1-2=7.8Hz,H-1"); 4.86 (s,2H,4'-ArOCH$_2$); 4.83 (m,1H,J=3.5Hz,J=3.0Hz,H-4); 4.69 (q,1H,J7-CH$_3$=4.9Hz,H-7"); 4.58 (d,1H,J1-2=5.3Hz, H-1); 4.56 (7AB,2H,J=16.5Hz,J6.6Hz, ArOCH$_2$); 4.39 (dd,1H,J=8.9Hz,J=10.5Hz,H-3a(A)); 4.37 (dAB,1H, J-16,4Hz,ArOCHA); 4.22 (t,1H,J=8.20Hz,H-3a (B)); 4.20 (m,1H,H-6"B); 4.15 (dAB,1H,J=16.3Hz, ArOCHB—); 3.66 (s,6H,OCH$_3$); 3.59 (t,1H,JAB=10.2Hz, H-6"B); 3.52 (t,1H,J4"-5"=9.45Hz,H-4"); 3.42 (ddd,1H,J5"-6"=4.8Hz, J5"-4"=9.45Hz,H-5"); 3.15 (dd,1H,J2-3=14.1Hz, J2-1=5.20Hz,H-2); 2.85 (m,1H,H-3); 1.35 (d,3H,JCH$_3$-7"= 5.0Hz,CH$_3$).

Anal. $C_{53}H_{47}FO_{19}$

|  | C | H |
|---|---|---|
| Calc. % | 60.92 | 4.53 |
| Fnd. % | 59.34 | 4.42 |

EXAMPLE 15

4'-(4-benzyl(phenoxyoxyacetyl)-4'-demethyl-4-O-[2,3-bis(4-benzyloxyphenoxyacetyl)-4,6-ethylideneglucosyl]epipodophyllotoxin The procedure of Example 1 was repeated, but using 2,3-bis(4-benzyloxyphenoxyacetyl)-4,6-ethylidene-β-D-glucose and 4'-(4-benzyloxyphenoxyacetyl)-4'-demethylepipodophyllotoxin, originating in a manner similar to Example 14, to obtain the desired product, isolated by chromatography as an amorphous powder.

IR (Nujol, $\nu$ cm$^{-1}$): 1760, 1690, 1590, 1490, 1200, 1055, 710.

$^1$H NMR (400 MHz, $CDCl_3$) δ ppm: 7.45–7.22 (m,15H, Ph); 6.92–6.70 (m,10H); 6.68 (1,1H,H-5); 6.50 (d,2H, J=9.1Hz); 6.38 (s,1H,H-8); 6.18(s,2H,H-2',H-6'); 5.80 (s,1H,OCHAO); 5.55 (d,1H,J=0.9Hz,OCHBO); 5.29 (t,1H, J=9.45Hz,H-3"); 4.97 (dd,1H,J=9.45Hz,H-3"); 4.97 (dd,1H, J=7.93Hz,J=9Hz,H-2"); 4.94 (s,2H,PhCH$_2$O-4'); 4.84 (d,1H,J=5.5Hz,H-1"); 4.84 (s,2H,PHCH$_2$O); 4.80 (qAB,2H, J=11.5Hz,PhCH$_2$O); 4.77 (s,2H,ArOCH$_2$-4'); 4.74 (d,1H,J4-3=3.5Hz,H-4); 4.61 (q,1H,J7-CH$_3$=5.0Hz,H-7"); 4.48 (d,1H,J1-2=6Hz,H-1); 4.47 (qAB,2H,J-16.5Hz, J=3.24Hz, ArOCH$_2$CO); 4.32 (t,1H,J=10.9Hz,J=8.6Hz,H-3a(A)); 4.30 (dAB,1H, J=16.5Hz,ArOCHβCO); 4.15 (t,1H, J=8.7Hz,H-3a(B)); 4.13 (dd,1H,JAB=10.26Hz,J6"-5"=4.7Hz, H-6"A); 4.04 (dAB,1H, J=16.4Hz,ArOCHACO); 3.56 (s,6H,OCH$_3$); 3.51 (t,1H,JAB=10.2Hz,H-6"B); 3.44 (t, 1H,J4"-5"=9.4Hz, H-4"); 3.35 (ddd,1H,J5"-4"=9.66Hz,J5"-6"=4.7Hz, H-5"); 3.08 (dd,1H,J2-3=14.1Hz,J2-1=5.2Hz, H-2); 2.75 (m,1H,H-3); 1.26 (d,3H,JCH$_3$-7"=5.0Hz,CH$_3$).

EXAMPLE 16

4'-(4-hydroxyphenoxyacetyl)-4'-demethyl-4-O-[2,3-bis(4-hydroxyphenoxyacetyl)-4,6-ethylideneglucosyl]epipodophyllotoxin 2.27 g of 4'-(4-benzyloxyphenoxyacetyl)-4'-demethyl-4-O-[2,3-bis(4-benzyloxyphenoxyacetyl)-4,6-ethylidene] epipodophyllotoxin originating from Example 15, dissolved in 25 ml of ethyl acetate, are hydrogenated in the presence of 0.9 g of 10% Pd/C at 50 psi for 8 h. The medium is filtered and evaporated under reduced pressure. The debenzylation product is then chromatographed on a silica column with an eluent of $CH_2Cl_2/MeOH$, 97:3. 1.40 g are obtained, equivalent to an 80% yield. M.p.=163° C.

IR (Nujol, $\nu(cm^{-1})$): 3360, 1745, 1500, 1200, 1070, 820, 710.

$^1$H NMR (400 MHz,$CD_3COCD_3$) δ ppm: 8.0 (s,1H,OH); 7.96 (s,1H,OH);7.95 (s,1H,OH); 7.09 (s,1H,H-5); 6.86 (d,2H,J=9.0Hz,Ar); 6.77 (d,2H,J=9.0Hz,Ar); 6.74 (m, 6H,Ar); 6.59 (d,2H,J=8.9Hz,Ar); 6.55 (s,1H,H-8); 6.40 (s,2H,H-2',H-6'); 5.98 (d,1H,J=0.8Hz,OCHAO); 5.84 (s,1H, OCHBO); 5.40 (t,1H,J3"-2"=9.2Hz,H-3"); 5.35 (d,1H,J= 7.9Hz,H-1"); 5.09 (d,1H,J4-3=3.3Hz,H-4); 5.0 (dd,1H,J2"-1"=7.9Hz,J2"-3"=9.4Hz,H-2"); 4.85 (s,2H,ArOCH$_2$CO-4'); 4.80 (q,1H,J7"-CH$_3$=5.0Hz,H-7"); 4.63 (d,1H,J1-2=5.3Hz, H-1); 4.59 (s,2H,ArOCH$_2$CO); 4.43 (dAB,1H,J=16.5Hz, ArOCHACO); 4.37 (dd,1H,J=10.1Hz,J=8.7Hz, H-3a(A)); 4.27 (dd,1H,J=8.3Hz,J=7.6Hz,H-3a(B)); 4.21 (m,1H,H-6"A); 4.06 (dAB,1H,J=16.6Hz,ArOCHBCO); 3.67 (m,OCH$_3$,H-6"B,H-4"); 3.57 (m,1H,H-5"); 3.19 (dd, 1H,J2-3=14.3Hz,J2-1=5.3Hz,H-2); 3.07 (m,1H,H-3); 1.26(d,3H, JCH$_3$-7"=5.06Hz,CH$_3$).

Anal. $C_{52}H_{50}O_{22}$

|  | C | H |
|---|---|---|
| Calc. % | 60.82 | 4.91 |
| Fnd. % | 60.78 | 4.96 |

EXAMPLE 17

4'-demethyl-4-O-[2,3-bis(phenoxyacetyl)-4,6-ethylideneglucosyl]epipodophyllotoxin 1st stage: Condensation of the glycosyl portion with the epipodophyllotoxin portion protected at position 4'.

Synthesis of 4'-benzyloxycarbonyl-4'-demethyl-4-O-[2,3-bis(phenoxyacetyl)-4,6-ethylideneglucosyl]epipodophyllotoxin BF$_3$ etherate (2.9 ml, 2.5 eq.) is added over 30 min to a solution, stirred at −18° C. and maintained under nitrogen, of 5 g (9.35 mmol) of 4'-benzyloxycarbonyl-4'-demethylepipodophyllotoxin and 2,3-bis(phenoxyacetyl)-4,6-ethylidene-β-D-glucose (6.65 g, 1.5 eq., 14 mmol) in 50 ml of anhydrous $CH_2Cl_2$. After 2 h of stirring at −18° C., the reaction is stopped by adding 3 ml of pyridine, and the organic phase is washed with water, dried over magnesium sulfate and concentrated under reduced pressure. After chromatography on silica gel (eluent $CH_2Cl_2$), 8.13 g of the glucosyl derivative are obtained in the amorphous state (Yld=88%).

2nd stage: Hydrogenolysis of position 4'.

5 g of glucosyl derivative obtained in the first stage, in 50 ml of anhydrous acetone, are placed in a hydrogenation vessel in the presence of 500 mg of 10% Pd/C. After the vessel has been securely connected to a hydrogen inlet, the solution is stirred magnetically and hydrogen is introduced at an excess pressure of 0.1013 bar (0.1 atmosphere); stirring is maintained for 2 h. After removal of the catalyst by filtration and evaporation of the solvent under reduced pressure, 4.32 g (quantitative Yld) of product are obtained in the amorphous state.

The analytical study gave the following results:

IR (Nujol) (, cm$^{-1}$): 1760 (c=o), 1600, 1050.

$^1$H NMR (400 MHz, CDCl$_3$) δ ppm: 6.7–7.3 (8H, m, Ar); 6.77 (1H, s, H-5); 6.73 (2H, d, Ar H); 6.49 (1H, s, H-8); 6.24 (2H, s, H-2',6'); 5.9 and 5.64 (2H,2d, OCH$_2$O); 5.43 (1H,s, phenol OH); 5.37 (1H,t,J=9.5Hz, H-3"); 5.05 (1H,dd,H-2"); 4.93 (1H,d,J=7.9Hz,H-1"); 4.82 (1H,d,J=3.4Hz,H-4); 4.69 (1H,q,H-7"); 4.60 (2H, m,OCH$_2$CO); 4.55 (1H,H-1); 4.40 and 4.18 (2H,2d, OCH$_2$CO); 4.39 (1H,dd,H-3a(A)); 4.18 (2H,m,H-3a(B) and H-6"eq.); 3.75 (6H,s,OCH$_3$); 3.59 (1H, t,H-6"ax); 3.52 (1H,m,H-4"); 3.44 (1H,m,H-5"); 3.15 (1H, dd,J2-1=5.2Hz, J2-3=14.1Hz,H-2); 2.87 (1H,m,H-3); 1.35 (1H,d, J=5.1Hz).

EXAMPLE 18

4'-demethyl-4-O-[2,3-bis(4-methoxyphenoxyacetyl)-4,6-ethylideneglucosyl]epipodophyllotoxin 1st stage: The procedure of Example 17 was repeated, but using 2,3-bis(4-methoxyphenoxyacetyl)-4,6-ethylidene-β-D-glucose and 4'-benzyloxycarbonyl-4'-demethylepipodophyllotoxin, to obtain the desired intermediate product 4'-benzyloxycarbonyl-4'-demethyl-4-O-[2,3-bis(4-methoxyphenoxyacetyl)-4'-ethylideneglucosyl) epipodophyllotoxin, the characteristics of which are as follows: Amorphous; Yld. 100%.

IR (Nujol) (v, cm$^{-1}$): 1750, 1590, 1220, 1020.

$^1$H NMR(400 MHz, CDCl$_3$), δ, ppm: 7.32–7.42 (m,5H, Ph); 6.86 (m,8H,ArO-5); 6.66 (d,2H,Ar); 6.48 (s,1H,H-8); 6.25 (s,2H,H-2',H-6'); 5.90 (s,1H,OCHAO); 5.67 (s, 1H,OCHBO); 5.35 (t,1H,J=9.4Hz,H-3"); 5.24 (s,2H, PhCH$_2$); 5.04 (dd,1H,J=7.9Hz J=9.2Hz,H-2"); 4.91 (d,1h, J=7.8Hz,H-1"); 4.81 (d,1H,J=3.4Hz,H-4); 4.68 (q,1H, J=4.9Hz,H-7"); 4.55 (d,1H,J=5.15Hz,H-1); 4.54 (qAB,2H, J=4.15Hz,J=16.5Hz,ArOCH$_2$); 4.38 (dd,1H,J=10.2Hz, J=9.2Hz,H-3a(A)); 4.36 (d,1H,J=16.4Hz,ArOCHA); 4.20 (m,2H,H-6"A,H3a(B)); 4.11 (d,1H,J=16.4Hz,ArOCHB); 3.71 (s,3H,CH$_3$OPh); 3.68 (s,3H,CH$_3$OPh); 3.65 (s,6H, OCH$_3$); 3.58 (t,1H,J=10.2Hz,H-6"B); 3.51 (t,1H, J=9.4Hz, H-4"); 3.42 (ddd,1H,J5"-4"=9.5Hz,J5"-6"=5.0Hz, H-5"); 3.15 (dd,1H,J=5.2Hz,J=14.2Hz,H-2); 2.83 (m,1H,H-3); 1.34 (d,3H,J=4.95Hz,CH$_3$).

2nd stage: Hydrogenolysis of position 4'

This intermediate protected at position 4' (1 g) is subjected to a hydrogenolysis in 30 ml of a 4:1 ethanol/acetone mixture containing 0.18 g of 10% Pd/C under a hydrogen atmosphere at ambient temperature and pressure with good stirring, for 2 h. After monitoring by TLC (eluent CH$_2$Cl$_2$/MeOH 97:3), the catalyst is filtered off on sintered glass and washed with ethanol. The filtrate is evaporated under reduced pressure to yield the compound the physical characteristics of which are as follows:

Crystals, M.p.=196° C.; Yld=100%; IR (Nujol ; v, cm$^{-1}$); 3400, 1750, 1590, 700.

1H NMR, 400 MHz, CDCl$_3$ (δ, ppm): 6.79 (m,5H,ArO, H-5); 6.76(d,2H,J=7.67Hz,J=9.0Hz,ArO); 6.67(d,2H,J= 9.0Hz, ArO); 6.49 (s,1H,H-8); 6.23 (s,2H,H-2',H-6'); 5.92 (d,1H,J=1.1Hz,OCHAO); 5.69 (d,1H,J=1.1Hz,OCHBO); 5.41 (s,1H,OH); 5.36 (t,1H,J3"-2"=9.4Hz,H-3"); 5.05 (dd, 1H,J2"-1"=7.92Hz,J2"-3"=9.25Hz,H-2"); 4.91 (d,1H, J1"-2"=7.82Hz,H-1"); 4.82 (d,1H,J4-3=3.4Hz,H-4); 4.69 (q,1H, J=5.0Hz,H-7"); 4.54 (qAB,2H,J=16.4Hz,J=4.3z, ArOCH$_2$); 4.53 (d,1H,H-1); 4.38 (dd,1H,J=8.84Hz, J=10.6Hz,H-3a(A) ); 4.37 (d,1H,J=16.4Hz,ArOCHA); 4.20 (m,2H,H-6"A,H-3a (B)); 4.12 (d,1H,J=16.4Hz,ArOCHB); 3.75 (s,6H,OCH$_3$); 3.71 (s,3H,CH$_3$O-PhOCH$_2$); 3.68 (s3H, CH$_3$O-PhOCH$_2$); 3.59 (t,1H,J=10.1Hz,H-6"B); 3.51 (t,1H, J=9.5Hz,H-4"); 3.42 (ddd,1H,J=4.7Hz,J=9.6Hz,H-5"); 3.13 (dd,1H,J2-1= 5.2Hz,J2-3=14.1Hz,H-2); 2.87 (m,1H, H-3); 1.34(d,3H,J= 4.98Hz,CH$_3$).

Anal. C$_{47}$H$_{48}$O$_{19}$

|  | C | H |
|---|---|---|
| Calc. % | 61.56 | 5.27 |
| Fnd. % | 61.40 | 5.19 |

EXAMPLE 19

4'-demethyl-4-O-[2,3-bis(4-fluorophenoxyacetyl)-4,6-ethylideneglucosyl]epipodophyllotoxin 1st stage: The procedure of Example 17 was repeated, but using 2,3-bis(4-fluorophenoxyacetyl)-4,6-ethylidene-β-D-glucose and 4'-benzyloxycarbonyl-4'-demethylepipodophyllotoxin, to obtain the desired intermediate: 4'-benzyloxycarbonyl-4'-demethyl-4-O-[2,3-(4-fluorophenoxyacetyl)-4,6-ethylideneglucosyl] epipodophyllotoxin, the characteristics of which are as follows:

Amorphous, Yld.: 98%; IR (Nujol, v, cm$^{-1}$): 1750, 1590, 1180, 705.

1H NMR (400 MHz, CDCl$_3$), (δ, ppm): 7.42–7.32 (m,5H, Ph); 6.93 (m,4H,F-Ph); 6.80 (m,2H,F-Ph); 6.77 (s,1H,H-5); 6.67 (m,2H,F-Ph); 6.51 (s,1H,H-8); 6.25 (s,2h,H-2',H-6'); 5.92 (d,1H,J=1.12Hz,OCHAO); 5.71 (d,1H,J=0.92Hz, OCHBO); 5.34 (t,1H,J3"-2"=9.4Hz,H-3"); 5.25 (s,2H, PhCH$_2$); 5.03 (dd,1H,J2"-1"=7.9Hz, J2"-3"=9.2Hz,H-2"); 4.91 (d,1H,J1"-2"=7.8Hz,H-1"); 4.83 (d,1H,J=3.4Hz,H-4); 4.69 (q,1H,J=5.0Hz,H-7"); 4.57 (d,1H,H-1); 4.55 (qAB,2H, J=16.5Hz,J=67Hz,ArOCH$_2$); 4.39 (dd,1H,J=10.5Hz,J= 8.7Hz,H-3a(A)); 4.37 (dAB,1H, J=16.3Hz,ArOCHA); 4.21 (m,2H,H-6"A, H-3a(B)); 4.15 (dAB,1H,J=16.4Hz, ArOCHB); 3.66 (s,6H,OCH$_3$); 3.59 (t,1H,J=1 0.2Hz,H-6"B); 3.52 (t,1H,J4"-5"=9.45Hz, H-4"); 3.42 (ddd,1H,J5"-4"=9.54Hz,J5"-6"=4.8Hz,H-5"); 3.15 (dd,1H,J=14.1Hz,J2-1=5.2Hz,H-2); 2.85 (m,1H,H-3); 1.35 (d,3H,J=5.0Hz,CH$_3$).

2nd stage: Hydrogenolysis of position 4'

This intermediate protected at position 4' is subjected to a hydrogenolysis on Pd/C as described in Example 18, to yield the compound the physical characteristics of which are as follows:

Crystals M.p.=164° C., Yld=94%; IR (Nujol, v(cm$^{-1}$)): 3400, 1755, 1595, 1170.

1H NMR, 400 MHz, CDCl$_3$, (δ, ppm): 6.93 (m,4H,ArO); 6.79 (m,2H,ArO); 6.76 (s,1H,H-5); 6.66 (m,2H,ArO); 6.51 (s,1H,H-8); 6.23 (s,2H,H-2',H-6'); 5.92 (d,1h, J=0.97Hz, OCHAO); 5.71 (d,1H,J=0.98Hz, OCHBO); 5.41 (s,1H,OH); 5.34 (t,1H,J3"-2"=9.4Hz,H-3"); 5.03 (dd, 1H,J2"-1"=7.9Hz, JZ"-3"=9.1Hz,H-2"); 4.92 (d,1H, J1"-2"=7.8Hz,H-1"); 4.83 (d,1H,J4-3=3.4Hz,H-4); 4.69 (q,1H,J7"-CH$_3$=4.9Hz,H-7"); 4.56 (qAB,2H,J-6.6Hz, J=16.5Hz,ArOCH$_2$); 4.54 (d,1H,J1-2=4.86Hz,H-1); 4.38 (t,1H,J=8.9Hz,J=10.3Hz,H-3a(A)); 4.375 (d,1H, J=16.5Hz,ArOCHA—); 4.21 (m,2H,H-3a(B), H-6"A); 4.15 (d,1H,J=16.4Hz,ArOCHB); 3.76 (s,6H, OCH$_3$); 3.59 (t,1H, JAB=10.1Hz,H-6"B); 3.52 (t,1H,J4"-3"=9.4Hz,H-4"); 3.42 (ddd,1h,J5"-6"=4.75Hz,J5"-4"= 9.6Hz,H-5"); 3.12 (dd,1h,J2-3=14.1Hz,J2-1=5,2Hz,H-2); 2.87 (m,1H,H-3); 1.35 (d,3H,JCH$_3$-7"=4.98Hz,CH$_3$).

Anal. $C_{45}H_{42}F_2O_{17}$

|  | C | H |
|---|---|---|
| Calc. % | 60.54 | 4.74 |
| Fnd. % | 60.55 | 4.73 |

EXAMPLE 20

4'-demethyl-4-O-[2,3-bis(4-hydroxyphenoxyacetyl) -4,6-ethylideneglucosyl]epipodophyllotoxin 1st stage: Condensation of the glucosyl portion and the epipodophyllotoxin portion.

The procedure of Example 17 was repeated, but using 2,3-bis(4-benzyloxyphenoxyacetyl)-4,6-ethylidene-β-D-glucose and 4'-benzyloxycarbonyl-4'-demethylepipodophyllotoxin, to obtain the desired intermediate: 4'-benzyloxycarbonyl-4'-demethyl-4-O-[2,3-bis(4'-benzyloxyphenoxyacetyl)-4,6-ethylideneglucosyl] epipodophyllotoxin, the characteristics of which are as follows:

Amorphous, Yld=98%; IR (Nujol, v (cm$^{-1}$)): 1750, 1590, 1490, 1200, 1070, 810, 715.

$^1$H NMR (400MHz, CDCl$_3$) δ ppm: 7.44–7.20 (m,Ph); 6.85–6.70 (m,OArO); 6.68 (s,1H,H-5); 6.59 (d,2H,J=9.1Hz, OArO); 6.38 (s,1H,H-8); 6.18 (s,2H,H-2',H-6'); 5.79 (s,1H, OCHAO); 5.55 (s,1H,OCHBO); 5.28 (t,1H, J=9.45Hz,H-3"); 5.17 (s,2H,PhCH$_2$); 4.97 (dd,1H, J2"-1"=7.9Hz,J2"-3"= 9Hz,H-2"); 4.84 (d,1H,J1"-2"=7Hz H-1"); 4.83 (s,2H, PhCH$_2$); 4.79 (qAB,2H,J=5.1Hz, J=11.6Hz,PhCH$_2$OArO); 4.74 (d,1H,J4-3=3.4Hz,H-4); 4.61 (q,1H,J=5.0Hz,H-7"); 4.50 (d,1H,J1-2=6.1Hz,H-1); 4.47 (qAB,2H,J=16.5Hz,J= 3.3Hz,ArOCH$_2$CO); 4.32 (dd,1H, J=10.5Hz, J=8.8Hz,H-3a (A)); 4.29 (dAB,1H,J=16.5Hz, ArOCHBCO); 4.14 (t,1H, J=8.2Hz,H-3a(B)); 4.12 (dd, 1H,J=4.78Hz,J=10.4Hz,H-6"A); 4.04 (dAB,1H,J=16.4Hz, ArOCHACO); 3.48 (s,6H, OCH$_3$); 3.51 (t,1H,J=10.1Hz, H-6"B); 3.44 (t,J=4"-3"= 9.4Hz,H-4"); 3.35 (ddd,1H, J5"-4"=9.6Hz,J5"-6"=4.7Hz,H-5"); 3.08 (dd,1H,J=5.2Hz, J-14,1Hz,H-2); 2.76 (m,1H,J= 10.9Hz,J=3.1Hz,H-3); 1.26 (d,3H,J=5.0Hz,CH$_3$).

2nd stage: Hydrogenolysis of position 4'

A solution of 1.5 g of the intermediate originating from the 1st stage, in 15 ml of distilled ethyl acetate containing 0.6 g of 10% Pd/c, is hydrogenated at 3.45 bars (50 psi) at room temperature for 24 h with good stirring. After TLC monitoring (eluent CH$_2$Cl$_2$MeOH, 95:5), the catalyst is filtered off, and the filtrate is evaporated under reduced pressure and chromatographed on a silica column (eluent CH$_2$Cl$_2$/MeOH, 97:3). The product (940 mg) is obtained in the form of crystals, M.p.=16° C., Yld=85%. The physical characteristics are as follows:

IR (Nujol, v, cm$^{-1}$): 3400, 1755, 1600, 1500, 1200, 1080.

NMR (400 MHz, CDCl$_3$) δ ppm: 6.93–6.61 (m,6H, OArO); 6.60 (s,1H,H-5); 6.55 (d,2H,J=9.0Hz,OArO); 6.41 (s,1H, H-8); 6.15 (s,2H,H-2',H-6'); 5.85 (s,1H,OCHAO); 5.66 (s,1H,OCHBO); 5.37 (s,1H,ArOH); 5.27 (t,1H,J3"-2"= 9.4Hz, H-3"); 5.01 (s,1H,OH); 4.95 (dd,1H,J2"-1"=7.8Hz, J2"-3"=9.2Hz,H-2"); 4.81 (d,1H,J=7.8Hz,H-1"); 4.75 (d,1H, J4-3.3Hz,H-4); 4.62 (q,1H,J7"-CH$_3$=4.9Hz, H-7"); 4.46 (qAB,2H,J=16.5Hz,J=7.4Hz,ArOCH$_2$CO); 4.40 (d,1H,J= 5Hz,H-1); 4.30 (dd,1H,J=10.5Hz,J=8.7Hz,H-3a (A)); 4.25 (dAB,1HJ=16.4Hz,ArOCHACO); 4.14 (m,2H, H-6"A,H-3a (B)); 4.01 (dAB,1H,J=16.4Hz,ArOCHBCO); 3.67 (s,6H, OCH$_3$); 3.52 (t,1H,J=10.2Hz,H-6"B); 3,44 (t,1H, J4"-3"= 9.4Hz,H-4"); 3.35 (ddd,1H,J5"-4"=9.5Hz,J5"-6"=4.7Hz); 3.0 (dd,1H,J2-3=14.0Hz,J2-1=5.2Hz,H-2); 2.79 (m,1H,H-3); 1.27 (d,3H,JCH$_3$-7"=4.97Hz,CH$_3$).

Anal. $C_{45}H_{44}O_{19}$

|  | C | H |
|---|---|---|
| Calc. % | 60.81 | 4.99 |
| Fnd. % | 60.23 | 5.06 |

EXAMPLE 21

4'-demethyl-4-O-[2,3-bis(4-benzyloxyphenoxyacetyl) -4,6-ethylideneglucosyl] epipodophyllotoxin A solution of 0.72 g of 4'-benzyloxycarbonyl-4'-demethyl-4-O-[2,3-bis(4-benzyloxyphenoxyacetyl)-4,6-ethylideneglucosyl]epipodophyllotoxin originating from the 1st stage of Example 20, in 10 ml of an ethanol/acetone (1:1) mixture containing 0.14 g of 10% Pd/C catalyst, is hydrogenated at atmospheric ambient temperature for 1 h. After monitoring by TLC (eluent CH$_2$Cl$_2$/MeOH, 97:3), the catalyst is filtered off and the filtrate is evaporated under reduced pressure. The desired product is purified by chromatography on silica (eluent CH$_2$Cl$_2$/MeOH, 99:1) and obtained in a 38% yield. M.p.=159° C.

The physical characteristics are as follows:

IR (Nujol, v (cm$^{-1}$)): 3440, 1750, 1590, 1490, 1200, 1075, 710, 690.

$^1$H NMR (400MHz, CDCl$_3$) δ ppm: 7.30–7.20 (m,10H, Ph); 6.79–6.70 (m,6H,OArO); 6.68 (s,1H,H-5); 6.60 (dm, J=9.0Hz,OArO); 6.38 (s,2H,H-2',H-6'); 5.80 (d,1H, J=0.75Hz,OCHAO); 5.56 (d,1H,J=0.75Hz,OCHBO); 5.33 (s, 1H,PhOH-4'); 5.29 (s,1H,J3"-2"=9.2H3,J3"-4"=9.4Hz, H-3"); 4.98 (dd,1H,J2"-1"=7.9Hz,J2"-3"=9.2Hz,H-2"); 4.84 (d,1H,J=7.6Hz,H-1"); 4.83 (s,2H,PhCH$_2$); 4.80 (qAB,2H,J= 11.6Hz,J=5.0Hz,PhCH$_2$OArO); 4.75 (d,1H,J43=3.4Hz,H-4); 4.61 (q,1H,J7"-CH$_3$=4.9Hz,H-7"); 4.47 (qAB,2H,J= 16.5Hz, J=3.4Hz,ArOCH$_2$CO); 4.45 (d,H,J=7Hz,H-1); 4.31 (dd,1H,J=8.96Hz,H-3a(A)); 4.30 (dAB,1H,J=16.3Hz, ArOCHACO); 4.13 (t,1H,jAB=8.1Hz, H-3a(B)); 4.125 (dd, 1H,JAB=10.6Hz,J6"-5"=4.7Hz,H-6"A); 4.05 (dAB,1H,J= 16.4Hz,ArOCHB CO); 3.67 (s,6H,OCH$_3$); 3.51 (t,1H,JAB= 10.1Hz,H-6"B); 3.44 (t,1H,J4"-5"=J4"-3"=9.4Hz, H-4"); 3.35 (ddd,1H,J5"-4"=9.4Hz,J5"-6"=4.7Hz, H-5"); 3.06 (dd, 1H,J2-3=14Hz,J2-1=5.1Hz,H-); 2.79 (m,1H,H-3); 1.265 (d,3H,JCH$_3$-7"=4.96Hz,CH$_3$).

Anal. $C_{59}H_{57}O_{19}$

|  | C | H |
|---|---|---|
| Calc. % | 66.22 | 5.37 |
| Fnd. % | 66.26 | 5.32 |

The compounds of formula I below were prepared according to the same procedure as the examples above:

4'-demethyl-4-O-[2,3-bis(4-methylphenoxyacetyl)-4,6-ethlideneglucosyl]epipodophyllotoxin (M.p.=130° C., TLC (SiO$_2$): Hept/AcOEt (40:60) Rf=0.35);

4'-demethyl-4-O-[2,3-bis(3,4,5-trimethoxyphenoxyacetyl)-4,6-ethylideneglucosyl]epipodophyllotoxin (M.p.=234° C. TLC (SiO$_2$): Hept/AcOEt (30:70) Rf=0.2);

4'-demethyl-4-O-[2,3-bis(3,4-methylenedioxyphenoxyacetyl)-4,6-ethylideneglucosyl]

epipodophyllotxin (M.p.=173° C., TLC (SiO$_2$): Hept/ AcOEt (30:70) Rf=0.35);

4'-demethyl-4-O-[2,3-bis(3,4-dimethoxyphenoxyacetyl)-4, 6-ethylideneglucosyl]epipodophyllotoxin (M.p.=194° C. TLC (SiO$_2$): CH$_2$Cl$_2$/MeOH (95:5) Rf=0.4);

4'-demethyl-4-O-[2,3-bis(4-(trifluoromethoxy) phenoxyacetyl)-4,6-ethylideneglucosyl] epipodophyllotoxin (M.p.=−116° C. TLC (SiO$_2$): Hept/ AcOEt (50:50) Rf=0.2);

4'-demethyl-(3,4,5-trimethoxyphenoxyacetyl)-4'-demethyl-4-O-[2,3-bis(3,4,5-trimethoxyphenoxyacetyl)-4,6-ethylideneglucosyl]epipodophyllotoxin (M.p.=130° C., TLC (SiO$_2$): Hept/AcOEt (50:50) Rf=0.4);

4'-(4-(trifluoromethoxy)phenoxyacetyl)-4'-demethyl-4-O-[2,3-bis(4-(trifluoromethoxy)phenoxyacetyl)-4,6-ethyl ideneglucosyl]epipodophyllotoxin (M.p.>260° C., TLC (SiO$_2$): Hept/AcOEt (30:70) Rf=0.4);

4'-(4-phenylphenoxyacetyl)-4'-demethyl-4-O-[2,3-bis(4-phenylpenoxyacetyl)-4,6-ethylideneglucosyl] epipodophyllotoxin (M.p.=130° C., TLC (SiO$_2$): Hept/ AcOEt (30:70) Rf=0.5);

4'-(2-naphthoxyacetyl)-4'-demethyl-4-O-[2,3-bis(2-naphthoxyacetyl) -4,6-ethylideneglucosyl] epipodophyllotoxin (M.p.=138° C., TLC (SiO$_2$): Hept/ AcOEt (30:70) Rf=0.35);

4'-(1-naphthoxyacetyl)-4'-demethyl-4-O-[2,3-bis(1-naphthoxyacetyl) -4,6-ethylideneglucosyl] epipodophyllotoxin (M.p.=125° C., TLC (SiO$_2$): Hept/ AcOEt (50:50) Rf=0.5);

4'-(cyclohexyloxyacetyl)-4'-demethyl-4-O-[2,3-bis (cyclohexyloxyacetyl)-4,6-ethylideneglucosyl] epipodophyllotoxin, (M.p.=160° C., TLC (SiO$_2$): Hept/ AcOEt (50:50) Rf=0.45);

4'-(4-methylphenoxyacetyl)-4'-demethyl-4-O-[2,3-bis(4-methylphenoxyacetyl)-4,6-ethylideneglucosyl] epipodophyllotoxin (M.p.=151° C., TLC (SiO$_2$): Hept/ AcOEt (50:50) Rf=0.4);

4'-(3,4-dimethoxyphenoxyacetyl)-4'-demethyl-4-O-[2,3-bis (3,4-dimethoxyphenoxyacetyl)-4,6-ethylideneglucosyl] epipodophyllotoxin (M.p.=158° C., TLC (SiO$_2$): Hept/ AcOEt (50:50) Rf=0.27);

4'-(3,4-methylenedioxyphenoxyacetyl)-4'-demethyl-4-O-[2, 3-bis(3,4-methylenedioxyphenoxyacetyl)-4,6-ethylideneglucosyl]epipodophyllotoxin (M.p.=158° C., TLC (SiO$_2$): Hept/AcOEt (20:80) Rf=0.26); with Hept for heptane, AcOEt for ethyl acetate and CH$_2$Cl$_2$ for methylene chloride.

BIOLOGICAL EXPERIMENTS

The compounds were tested in vitro and in vivo, and showed value as an anticancer agent in the following tests.

The colorimetric MTT test (applied according to the procedure described by the NCI) enabled the antitumor power of said compounds to be evaluated in vitro on 6 cell lines originating from the ATCC and including models of breast, bladder, lung, and colon cancers.

In vivo, two tests were used, namely p388 leukemia and MXT adenocarcinoma. The leukemic cells were injected i.p. into the animals on day D0. The latter were then treated with the compounds on days D1, D2, D3 and D4. MXT adenocarcinoma was transplanted s.c. on day D0. The animals were treated on days D17, D19, D21, D24, D26, D28, D31, D33 and D35. The "T/C" index was evaluated for these two mouse models. This index represents the ratio of the median survival of treated animals (T) relative to that of control animals (C). This T/C index is expressed as a %, and when its value exceeds 130%, the compound under study is defined as showing significant antitumor activity. When the value of T/C exceeds 300%, a second index, LS, is expressed, which represents the percentage of "Long Surviving" animals on D30. This is calculated only for the P388 model, since the MXT model is too aggressive and does not permit such LS animals to be obtained. Each experimental group contained 10 animals.

The results are presented in the following table:

| | IN VIVO EXAMPLES | |
|---|---|---|
| Etoposide | P388* T/C % (LS %) 65(0) | MXT T/C % 71* |
| 17 | >300(40) | 155* |
| 1 | >300(90) | 139** |
| 18 | >300(100) | 161** |
| 3 | >300(60) | 105* |
| 19 | >300(90) | 160** |
| 14 | >300(60) | 138** |
| 16 | >300(80) | 107** |
| 20 | >300(90) | 136** |

*4 treatments at 40 mg/kg
**9 treatments at 40 mg/kg

These products are very advantageous relative to the products known at the present time, since they display, besides activity against the different forms of cancer comprising, in particular, embryonic carcinomas of the testicle, connective tissue sarcomas, pediatric tumors, small cell bronchial cancers, Hodgkim's and non-Hodgkim's lymphomas, acute leukemias and breast cancers, activity against non-small cell cancers of the lung and colorectal cancers where therapy fails at the present time.

Hence the present invention also relates to the compounds of general formula I, including the compounds described in the prior art as synthesis intermediates and excluded by the disclaimer, as a medicinal product, as well as to their use for the preparation of a medicinal product intended for anticancer treatment, especially embryonic carcinomas of the testicle, connective tissue sarcomas, pediatric tumors, connective tissue sarcomas, pediatric tumors, small cell bronchial cancers, Hodgkim's and non-Hodgkim's malignant lymphomas, acute leukemias, placental choriocarcinomas, mammary adenomes carcinomas, colorectal cancers and non-small cell cancers of the lung.

It also relates to a pharmaceutical composition comprising at least one compound of general formula I, including the compounds described in the prior art as synthesis intermediates and excluded by the disclaimer, and a suitable excipient.

The pharmaceutical compositions can be in a form suitable for administration by injection in perfusion or oral administration in the form of hard gelatin capsules or tablets, at a dosage of 20 to 200 mg/m$^2$ for injection per 24 h and 50 to 400 mg/m$^2$ per 24 h for the oral form.

We claim:

1. Compound of general formula I:

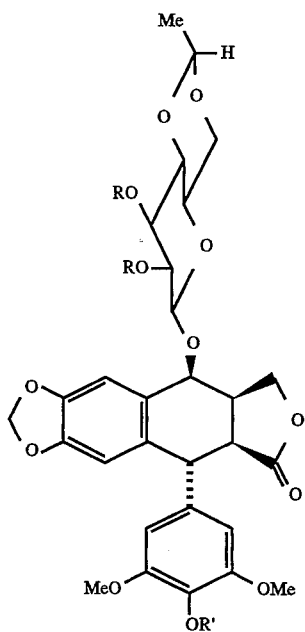

in which

R' represents a hydrogen atom or a radical R, and

R represents a group of formula

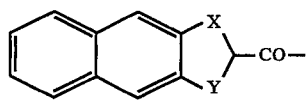

or an acyl residue of formula

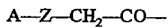

in which formulae

X, Y and Z independently represent an oxygen atom or a sulfur atom, and

A represents
- a linear or branched $C_1$–$C_4$ alkyl radical,
- a $C_3$–$C_6$ cycloalkyl radical,
- an aryl radical selected from the group consisting of phenyl, phenyl(linear or branched $C_1$–$C_4$ alkyl) and naphthyl radicals and these same radicals substituted with one to three substituents selected from the group consisting of hydroxyl radicals, linear or branched $C_1$–$C_4$ alkoxy radicals optionally perhalogenated with chlorine or fluorine atoms, benzyloxy, phenyl and linear or branched $C_1$–$C_4$ alkyl radicals and halogen atoms, or a physiologically acceptable salt thereof, on the condition that, when R' represents a radical R, R is selected from the group consisting of 4-fluorophenoxyacetyl, 4-benzyloxyphenoxyacetyl, 4-hydroxyphenoxyacetyl, 4-methylphenoxyacetyl, 3,4,5-trimethoxyphenoxyacetyl, 3,4-methylenedioxyphenoxyacetyl, 2,3-dimethoxyphenoxyacetyl, 4-(trifluoromethoxy)phenoxyacetyl, 4-phenylphenoxyacetyl, 2-naphthoxyacetyl, 1-naphthoxyacetyl, cyclohexylacetyl, 4-methylphenoxyacetyl and 3,4-dimethoxyphenoxyacetyl.

2. Compound according to claim 1, wherein R' represents a hydrogen atom.

3. Compound according to claim 1, characterized in that R is selected from the group consisting of ethoxyacetyl, phenoxyacetyl, 4-methoxyphenoxyacetyl, 2-methoxyphenoxyacetyl, 4-nitrophenoxyacetyl, 2-nitrophenoxyacetyl, 2,4-dichlorophenoxyacetyl, 2,4,5-trichlorophenoxyacetyl, 2,4,6-trichlorophenoxyacetyl, 4-fluorophenoxyacetyl, 2-fluorophenoxyacetyl, 4-hydroxyphenoxyacetyl, 4-benzyloxyphenoxyacetyl, 4-methylphenoxyacetyl, 3,4,5-trimethoxyphenoxyacetyl, 3,4-methylenedioxyphenoxyacetyl, 2,3-dimethoxyphenoxyacetyl, 4-(trifluoromethoxy)phenoxyacetyl, 4-phenylphenoxyacetyl, 2-naphthoxyacetyl, 1-naphthoxyacetyl, cyclohexylacetyl, 4-methylphenoxyacetyl and 3,4-dimethoxyphenoxyacetyl.

4. Compound according to claim 1, in that it is selected from the group consisting of:

4'-(4-fluorophenoxyacetyl)-4'-demethyl-4-O-[2,3-bis(4-fluorophenoxyacetyl)-4,-ethylideneglucosyl] epipodphyllotoxin, 4'-(4-benzyloxyphenoxyacetyl)-4'-demethyl-4-O-[2,3-bis(4-benzyloxyphenoxyacetyl)-4,6-ethylideneglucosyl] epipodophyllotoxin, 4'-(4-hydroxyphenoxyacetyl)-4'-demethyl-4-O-[2,3-bis(4-hydroxyphenoxyacetyl)-4,6-ethylideneglucosyl] epipodophyllotoxin, 4'-demethyl-4-O-[2,3-bis(phenoxyacetyl)-4,6-ethylideneglucosyl]epipodophyllotoxin, 4'-demethyl-4-O-[2,3-bis(4-methoxyphenoxyacetyl)-4,6-ethylideneglucosyl]epipodophyllotoxin, 4'-demethyl-4-O-[2,3-bis(4-fluorophenoxyacetyl)-4,6-ethylideneglucosyl]epipodophyllotoxin, 4'-demethyl-4-O-[2,3-bis(4-hydroxyphenoxyacetyl)-4,6-ethylideneglucosyl]epipodophyllotoxin, 4"-demethyl-4-O-[2,3-bis(4-benzyloxyphenoxyacetyl)-4,6-ethylideneglucosyl]epipodophyllotoxin, 4'-demethyl-4-O-[2,3-bis(4-methylphenoxyacetyl)-4,6-ethlideneglucosyl]epipodophyllotoxin), 4'-demethyl-4-O-[2,3-bis(3,4,5-trimethoxyphenoxyacetyl)-4,6-ethylideneglucosyl]epipodophyllotoxin, 4'-demethyl-4-O-[2,3-bis(3,4-methylenedioxyphenoxyacetyl)-4,6-ethylideneglucosyl] epipodophyllotoxin, 4'-demethyl-4-O-[2,3-bis(3,4-dimethoxyphenoxyacetyl)-4,6-ethylideneglucosyl]epipodophyllotoxin, 4'-demethyl-4-O-[2,3-bis(4-trifluoromethoxy)phenoxyacetyl)-4,6-ethylideneglucosyl] epipodophyllotoxin, 4'-(3,4,5-trimethoxyphenoxyacetyl)-4'-demethyl -4-O-2,3-bis(3,4,5-trimethoxyphenoxyacetyl) -4,6-ethylideneglucosyl]epipodophyllotoxin, 4'-(4-(trifluoromethoxy)phenoxyacetyl)-4'-demethyl-4-O-[2,3-bis (4-(trifluoromethoxy)phenoxyacetyl)-4,6-ethylideneglucosyl]epipodophyllotoxin, 4'-(4-phenylphenoxyacetyl)-4'-demethyl-4-O-[2,3-bis(4-phenylpenoxyacetyl)-4,6-ethylideneglucosyl] epipodophyllotoxin, 4'-(2-naphthoxyacetyl)-4'-demethyl-4-O-[2,3-bis(2-naphthoxyacetyl) -4,6-ethylideneglucosyl] epipodophyllotoxin 4'-(1-naphthoxyacetyl)-4'-demethyl-4-O-[2,3-bis(1-naphthoxyacetyl)-4,6-ethylideneglucosyl] epipodophyllotoxin, 4'-(cyclohexyloxyacetyl)-4'-demethyl-4-O-[2,3-bis(cyclohexyloxyacetyl) -4,6-ethylideneglucosyl] epipodophyllotoxin, 4'-(4-methylphenoxyacetyl)-4'-demethyl-4-O-[2,3-bis(4-methylphenoxyacetyl)-4,6-ethylideneglucosyl] epipodophyllotoxin, 4'-(3,4-dimethoxyphenoxyacetyl)-4'-demethyl-4-O-[2,3-bis (3,4-dimethoxyphenoxyacetyl)-4,6-ethylideneglucosyl] epipodophyllotoxin, and 4'-(3,4-methylenedioxyphenoxyacetyl)-4'-demethyl-4-O-[2, 3-bis(3,4-methylenedioxyphenoxyacetyl)-4,6-ethylideneglucosyl]epipodophyllotoxin.

5. As a pharmaceutical composition, the compound of formula I:

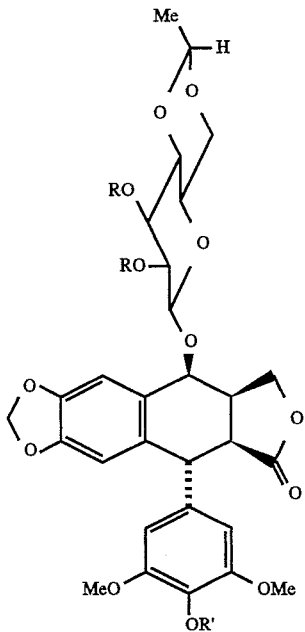

in which

R' represents a hydrogen atom or a radical R, and
R represents a group of formula

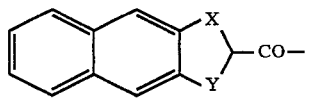

or an acyl residue of formula

in which formulae

X, Y and Z independently represent an oxygen atom or a sulfur atom, and

A represents a linear or branched $C_1$–$C_4$ alkyl radical, a $C_3$–$C_6$ cycloalkyl radical, an aryl radical selected from the group consisting of phenyl, phenyl(linear or branched $C_1$–$C_4$ alkyl) and naphthyl radicals and these same radicals substituted with one to three substituents selected from the group consisting of hydroxyl radicals, linear or branched $C_1$–$C_4$ alkoxy radicals optionally perhalogenated with chlorine or fluorine atoms, benzyloxy, phenyl and linear or branched $C_1$–$C_4$ alkyl radicals and halogen atoms, or a physiologically acceptable salt thereof together with a pharmaceutically acceptable excipient.

6. Pharmaceutical composition according to claim 1, characterized in that R' represents a hydrogen atom.

7. Pharmaceutical composition according to claim 5, characterized in that R is selected from the group consisting of ethoxyacetyl, phenoxyacetyl, 4-methoxyphenoxyacetyl, 2-methoxyphenoxyacetyl, 4-nitrophenoxyacetyl, 2-nitrophenoxyacetyl, 2,4-dichlorophenoxyacetyl, 2,4,5-trichlorophenoxyacetyl, 2,4,6-trichlorophenoxyacetyl, 4-fluorophenoxyacetyl, 2-fluorophenoxyacetyl, 4-hydroxyphenoxyacetyl, 4-benzyloxyphenoxyacetyl, 4-methylphenoxyacetyl, 3,4,5-trimethoxyphenoxyacetyl, 3,4-methylenedioxyphenoxyacetyl, 2,3-dimethoxyphenoxyacetyl, 4-(trifluoromethoxyphenoxyacetyl, 4-phenylphenoxyacetyl, 2-naphthoxyacetyl, 1-naphthoxyacetyl, cyclohexylacetyl, 4-methylphenoxyacetyl and 3,4-dimethoxyphenoxyacetyl.

8. Pharmaceutical composition according to claim 5, characterized in that the active ingredient selected from the group consisting of:

4'-phenoxyacetyl-4'-demethyl-4-O-[2,3-bis(phenoxyacetyl) -4,6-ethylideneglucosyl]epipodophyllotoxin, 4'-(2-methoxyphenoxyacetyl)-4'-demethyl-4-O-[2,3-bis(2-methoxyphenoxyacetyl)-4,6-ethylideneglucosyl] epipodophyllotoxin, 4'-(4-methoxyphenoxyacetyl)-4'-demethyl-4-O-[2,3-bis(4-methoxyphenoxyacetyl)-4,6-ethylideneglucosyl] epipodophyllotoxin, 4'-(2-nitrophenoxyacetyl)-4'-demethyl-4-O-[2,3-bis(2-nitrophenoxyacetyl)-4,6-ethylideneglucosyl] epipodophyllotoxin, 4'-(4-nitrophenoxyacetyl)-4'-demethyl-4-O-[2,3-bis(4-nitrophenoxyacetyl)-4,6-ethylideneglucosyl] epipodophyllotoxin, 4'-(2,4-dichlorophenoxyacetyl)-4'-demethyl-4-O-[2,3-bis(2, 4-dichlorophenoxyacetyl)-4,6-ethylideneglucosyl] epipodophyllotoxin, 4'-(2,4,5-trichlorophenoxyacetyl)-4'-demethyl-4-O-[2,3-bis (2,4,5-trichlorophenoxyacetyl)-4,6-ethylideneglucosyl] epipodophyllotoxin, 4'-(2,4,6-trichlorophenoxyacetyl)-4'-demethyl-4-O-[2,3-bis (trichlorophenoxyacetyl)-4,6-ethylideneglucosyl] epipodophyllotoxin, 4'-(2-fluorophenoxyacetyl)-4'-demethyl-4-O-[2,3-bis(2-fluorophenoxyacetyl)-4-ethylideneglucosyl] epipodophyllotoxin, 4'-ethoxyacetyl-4'-demethyl-4-O-[2,3-bis(ethoxyacetyl)-4, 6-ethylideneglucosyl]epipodophyllotoxin, 4'-[2,2-(2,3-naphthylidenedioxy)acetyl]-4'-demethyl -4-O-[2,3-bis[2,2-(2,3-naphthylidenedioxy)acetyl]-4,6-ethylideneglucosyl]epipodophyllotoxin, 4'-benzylthioacetyl-4'-demethyl-4-O-[2,3-bis (benzylthioacetyl)-4,6-ethylideneglucosyl] epipodophyllotoxin, 4'-phenylthioacetyl-4'-demethyl-4-O-[2,3-bis (phenylthioacetyl)-4,6-ethylideneglucosyl] epipodophyllotoxin, 4'-(4-fluorophenoxyacetyl)-4'-demethyl-4-O-[2,3-bis(4-fluorophenoxyacetyl)-4'-ethylideneglucosyl] epipodphyllotoxin, 4'-(4-benzyloxyphenoxyacetyl)-4'-demethyl-4-O-[2,3-bis (4-benzyloxyphenoxyacetyl)-4,6-ethylideneglucosyl] epipodophyllotoxin, 4'-(4-hydroxyphenoxyacetyl)-4'-demethyl-4-O-[2,3-bis(4-hydroxyphenoxyacetyl)-4,6-ethylideneglucosyl] epipodophyllotoxin, 4'-demethyl-4-O-[2,3-bis(phenoxyacetyl)-4,6-ethylideneglucosyl]epipodophyllotoxin, 4'-demethyl-4-O-[2,3-bis(4-methoxyphenoxyacetyl) -4,6-ethylideneglucosyl]epipodophyllotoxin, 4'-demethyl-4-O-[2,3-bis(4-fluorophenoxyacetyl)-4,6-ethylideneglucosyl]epipodophyllotoxin, 4'-demethyl-4-O-[2,3-bis(4-hydroxyphenoxyacetyl) -4,6-ethylideneglucosyl]epipodophyllotoxin, 4"-demethyl-4-O-[2,3-bis(4-benzyloxyphenoxyacetyl) -4,6-ethylideneglucosyl]epipodophyllotoxin, 4'-demethyl-4-O-[2,3-bis(4-methylphenoxyacetyl)-4,6-ethlideneglucosyl]epipodophyllotoxin), 4'-demethyl-4-O-[2,3-bis(3,4,5-trimethoxyphenoxyacetyl) -4,6-ethylideneglucosyl]epipodophyllotoxin, 4'-demethyl-4-O-[2,3-bis(3,4-methylenedioxyphenoxyacetyl) -4,6-ethylideneglucosyl]epipodophyllotoxin, 4'-demethyl-4-O-[2,3-bis(3,4-dimethoxyphenoxyacetyl) -4,6-ethylideneglucosyl]epipodophyllotoxin, 4'-demethyl-4-O-[2,3-bis(4-trifluoromethoxy) phenoxyacetyl) -4,6-ethylideneglucosyl] epipodophyllotoxin, 4'-(3,4,5-trimethoxyphenoxyacetyl)-4'-demethyl-4-O-[2,3-bis(3,4,5-trimethoxyphenoxyacetyl)-4,6-ethylideneglucosyl]epipodophyllotoxin, 4'-(4-(trifluoromethoxy)phenoxyacetyl)-4'-demethyl -4-O-[2,3-bis(4-(trifluoromethoxy)phenoxyacetyl)-4,6-ethylideneglucosyl]epipodophyllotoxin, 4'-(4-phenylphenoxyacetyl)-4'-demethyl-4-O-[2,3-bis(4-phenylpenoxyacetyl)-4,6-ethylideneglucosyl] epipodophyllotoxin, 4'-(2-naphthoxyacetyl)-4'-demethyl-4-O-[2,3-bis(2-naphthoxyacetyl)-4,6-ethylideneglucosyl] epipodophyllotoxin, 4'-(1-naphthoxyacetyl)-4'-demethyl-4-O-[2,3-bis(1-naphthoxyacetyl)-4,6-ethylideneglucosyl] epipodophyllotoxin, 4'-(cyclohexyloxyacetyl)-4'-demethyl-4-O-[2,3-bis (cyclohexyloxyacetyl)-4,6-ethylideneglucosyl] epipodophyllotoxin, 4'-(4-methylphenoxyacetyl)-4'-demethyl-4-O-[2,3-bis(4-methylphenoxyacetyl)-4,6-ethylideneglucosyl] epipodophyllotoxin, 4'-(3,4-dimethoxyphenoxyacetyl)-4'-demethyl-4-O-[2,3-bis(3,4-dimethoxyphenoxyacetyl)-4,6-ethylidene-glucosyl]epipodophyllotoxin, and 4'-(3,4-methylenedioxyphenoxyacetyl)-4'-demethyl-4-O-[2, 3-bis(3,4-methylenedioxyphenoxyacetyl)-4,6-ethylideneglucosyl]epipodophyllotoxin.

9. Compound of claim 1 wherein halogen is chlorine or fluorine.

10. Pharmaceutical composition of claim 5 wherein halogen is chlorine or fluorine.

11. Method of treating a mammalian cancer comprising the step of administering to the mammal an effective anti-cancer amount of a compound of formula I:

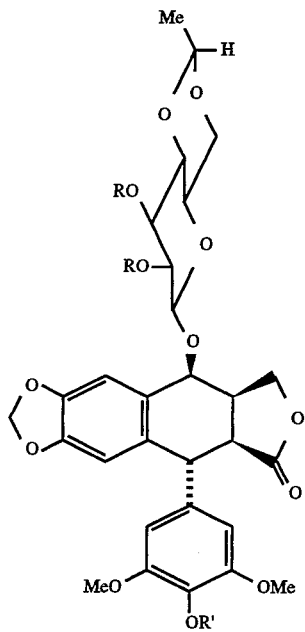

in which

R' represents a hydrogen atom or a radical R, and

R represents a group of formula

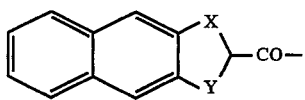

or an acyl residue of formula

A—Z—CH$_2$—CO— in which formulae

X, Y and Z independently represent an oxygen atom or a sulfur atom, and

A represents a linear or branched $C_1$–$C_4$ alkyl radical, a $C_3$–$C_6$ cycloalkyl radical, an aryl radical selected from the group consisting of phenyl, phenyl(linear or branched $C_1$–$C_4$ alkyl) and naphthyl radicals and these same radicals substituted with one to three substituents selected from the group consisting of hydroxyl radicals, linear or branched $C_1$–$C_4$ alkoxy radicals optionally perhalongenated with chlorine or fluorine atoms, benzyloxy, phenyl and linear or branched $C_1$–$C_4$ alkyl radicals and halogen atoms, or a physiologically-acceptable salt thereof.

12. Method according to claim 11, characterized in that R' represents a hydrogen atom.

13. Method according to claim 11, characterized in that R is selected from the group consisting of ethoxyacetyl, phenoxyacetyl, 4-methoxyphenoxyacetyl, 2-methoxyphenoxyacetyl, 4-nitrophenoxyacetyl, 2-nitrophenoxyacetyl, 2,4-dichlorophenoxyacetyl, 2,4,5-trichlorophenoxyacetyl, 2,4,6-trichlorophenoxyacetyl, 4-fluorophenoxyacetyl, 2-fluorophenoxyacetyl, 4-hydroxyphenoxyacetyl, 4-benzyloxyphenoxyacetyl, 4-methylphenoxyacetyl, 3,4,5-trimethoxyphenoxyacetyl, 3,4-methylenedioxyphenoxyacetyl, 2,3-dimethoxyphenoxyacetyl, 4-(trifluoromethoxyphenoxyacetyl, 4-phenylphenoxyacetyl, 2-naphthoxyacetyl, 1-naphthoxyacetyl, cyclohexylacetyl, 4-methylphenoxyacetyl and 3,4-dimethoxyphenoxyacetyl.

14. Method according to claim 11, characterized in that the compound is selected from the group consisting of:

4'-phenoxyacetyl-4'-demethyl-4-O-[2,3-bis(phenoxyacetyl)-4,6-ethylideneglucosyl]epipodophyllotoxin, 4'-(2-methoxyphenoxyacetyl)-4'-demethyl-4-O-[2,3-bis(2-methoxyphenoxyacetyl)-4,6-ethylideneglucosyl]epipodophyllotoxin, 4'-(4-methoxyphenoxyacetyl)-4'-demethyl-4-O-[2,3-bis(4-methoxyphenoxyacetyl)-4,6-ethylideneglucosyl]epipodophyllotoxin, 4'-(2-nitrophenoxyacetyl)-4'-demethyl-4-O-[2,3-bis(2-nitrophenoxyacetyl)-4,6-ethylideneglucosyl]epipodophyllotoxin, 4'-(4-nitrophenoxyacetyl)-4'-demethyl-4-O-[2,3-bis(4-nitrophenoxyacetyl)-4,6-ethylideneglucosyl]epipodophyllotoxin, 4'-(2,4-dichlorophenoxyacetyl)-4'-demethyl-4-O-[2,3-bis(2,4-dichlorophenoxyacetyl)-4,6-ethylideneglucosyl]epipodophyllotoxin, 4'-(2,4,5-trichlorophenoxyacetyl)-4'-demethyl-4-O-[2,3-bis(2,4,5-trichlorophenoxyacetyl)-4,6-ethylideneglucosyl]epipodophyllotoxin, 4'-(2,4,6-trichlorophenoxyacetyl)-4'-demethyl-4-O-[2,3-bis(trichlorophenoxyacetyl)-4,6-ethylideneglucosyl]epipodophyllotoxin, 4'-(2-fluorophenoxyacetyl)-4'-demethyl-4-O-[2,3-bis(2-fluorophenoxyacetyl)-4-ethylideneglucosyl]epipodophyllotoxin, 4'-ethoxyacetyl-4'-demethyl-4-O-[2,3-bis(ethoxyacetyl)-4,6-ethylideneglucosyl]epipodophyllotoxin, 4'-[2,2-(2,3-naphthylidenedioxy)acetyl]-4'-demethyl-4-O-[2,3-bis[2,2-(2,3-naphthylidenedioxy)acetyl]-4,6-ethylideneglucosyl]epipodophyllotoxin, 4'-benzylthioacetyl-4'-demethyl-4-O-[2, 3-bis(benzylthioacetyl)-4,6-ethylideneglucosyl]epipodphyllotoxin, 4'-phenylthioacetyl-4'-demethyl-4-O-[2,3-bis(phenylthioacetyl)-4,6-ethylideneglucosyl]epipodophyllotoxin, 4'-(4-fluorophenoxyacetyl)-4'-demethyl-4-O-[2,3-bis(4-fluorophenoxyacetyl)-4'-ethylideneglucosyl]epipodphyllotoxin, 4'-(4-benzyloxyphenoxyacetyl)-4'-demethyl-4-O-[2,3-bis(4-benzyloxyphenoxyacetyl)-4,6-ethylideneglucosyl]epipodophyllotoxin, 4'-(4-hydroxyphenoxyacetyl)-4'-demethyl-4-O-[2,3-bis(4-hydroxyphenoxyacetyl)-4,6-ethylideneglucosyl]epipodophyllotoxin, 4'-demethyl-4-O-[2,3-bis(phenoxyacetyl)-4,6-ethylideneglucosyl]epipodophyllotoxin, 4'-demethyl-4-O-[2,3-bis(4-methoxyphenoxyacetyl) -4,6-ethylideneglucosyl]epipodophyllotoxin, 4'-demethyl-4-O-[2,3-bis(4-fluorophenoxyacetyl)-4,6-ethylideneglucosyl]epipodophyllotoxin, 4'-demethyl-4-O-[2,3-bis(4-hydroxyphenoxyacetyl) -4,6-ethylideneglucosyl]epipodophyllotoxin, 4"-demethyl-4-O-[2,3-bis(4-benzyloxyphenoxyacetyl) -4,6-ethylideneglucosyl]epipodophyllotoxin, 4'-demethyl-4-O-[2,3-bis(4-methylphenoxyacetyl)-4,6-ethlideneglucosyl]epipodophyllotoxin), 4'-demethyl-4-O-[2,3-bis(3,4,5-trimethoxyphenoxyacetyl)-4,6-ethylideneglucosyl]epipodophyllotoxin, 4'-demethyl-4-O-[2,3-bis(3,4-methylenedioxyphenoxyacetyl) -4,6-ethylideneglucosyl]epipodophyllotoxin, 4'-demethyl-4-O-[2,3-bis(3,4-dimethoxyphenoxyacetyl) -4,6-ethylideneglucosyl]epipodophyllotoxin, 4'-demethyl-4-O-[2,3-bis(4-trifluoromethoxy) phenoxyacetyl) -4,6-ethylideneglucosyl]epipodophyllotoxin, 4'-(3,4,5-trimethoxyphenoxyacetyl)-4'-demethyl-4-O-[2,3-bis(3,4,5-trimethoxyphenoxyacetyl)-4,6-ethylideneglucosyl]epipodophyllotoxin, 4'-(4-(trifluoromethoxy)phenoxyacetyl)-4'-demethyl -4-O-[2,3-bis(4-(trifluoromethoxy)phenoxyacetyl)-4,6-ethylideneglucosyl]epipodophyllotoxin, 4'-(4-phenylphenoxyacetyl)-4'-demethyl-4-O-[2,3-bis(4-phenylpenoxyacetyl)-4,6-ethylideneglucosyl]epipodophyllotoxin, 4'-(2-naphthoxyacetyl)-4'-demethyl-4-O-[2,3-bis(2-naphthoxyacetyl)-4,6-ethylideneglucosyl]epipodophyllotoxin, 4'-(1-naphthoxyacetyl)-4'-demethyl-4-O-[2,3-bis(1-naphthoxyacetyl)-4,6-ethylideneglucosyl]epipodophyllotoxin, 4'-(cyclohexyloxyacetyl)-4'-demethyl-4-O-[2,3-bis(cyclohexyloxyacetyl)-4,6-ethylideneglucosyl]epipodophyllotoxin, 4'-(4-methylphenoxyacetyl)-4'-demethyl-4-O-[2,3-bis(4-methylphenoxyacetyl)-4,6-ethylideneglucosyl]epipodophyllotoxin, 4'-(3,4-dimethoxyphenoxyacetyl)-4'-demethyl-4-O-[2,3-bis(3,4-dimethoxyphenoxyacetyl)-4,6-ethylideneglucosyl]epipodophyllotoxin, and 4'-(3,4-methylenedioxyphenoxyacetyl)-4'-demethyl-4-O-[2,3-bis(3,4-methylenedioxyphenoxyacetyl)-4,6-ethylideneglucosyl]epipodophyllotoxin.

* * * * *

UNITED STATES PATENT AND TRADEMARK OFFICE
CERTIFICATE OF CORRECTION

PATENT NO. : 5,643,885
DATED : July 1, 1997
INVENTOR(S) : Jean-Pierre Robin, Robert Kiss, Thierry Imbert Page 1 of 3

It is certified that error appears in the above-indentified patent and that said Letters Patent is hereby corrected as shown below:

Column 4, lines 41 to 58, Delete these lines and make the corrections as follows:

Column 5, top left: The line should read
-- 4'-demethyl-4'OZ-epipodophyllotoxin --.

Column 6, at right above vertical arrow: should read
-- 4'-demethylepipodophyllotoxin --.

Column 6, at right, underneath the arrow: should read
-- 4'-demethyl-4'-phenoxy-
acetyl(epipodophyllotoxin)--.

Column 10, line 43: "demethylepipodophyllotixin" should read -- demethylepipodophyllotoxin --.

Column 13, line 65: Insert -- ); -- at the end of the line.

Column 13, line 66: Delete ");" at the beginning of the line.

Column 16, line 36: "=9.2H3," in the middle of the line, should read -- 9.2$H_3$," --.

Column 19, line 2: Delete the word "general".

UNITED STATES PATENT AND TRADEMARK OFFICE
CERTIFICATE OF CORRECTION

PATENT NO. : 5,643,885
DATED : July 1, 1997
INVENTOR(S) : Jean-Pierre Robin, Robert Kiss, Thierry Imbert Page 2 of 3

It is certified that error appears in the above-indentified patent and that said Letters Patent is hereby corrected as shown below:

Column 19, line 57: Insert a -- dash -- between physiologically" and "acceptable".

Column 20, line 17: Delete "in that it is".

Column 20, line 47: Insert -- [ -- before "2,3-" at the end of the line.

Column 21, line 7: Change the word "the" to -- a --.

Column 21, line 62: Insert a -- - -- (dash) between "physiologically" and "acceptable".

Column 21, line 63: Insert a -- - -- (dash) between "pharmaceutically" and "acceptable".

Column 23, line 54: After the word "cancer" Insert -- of a type treatable with etoposide --.

UNITED STATES PATENT AND TRADEMARK OFFICE
CERTIFICATE OF CORRECTION

PATENT NO. : 5,643,885
DATED : July 1, 1997
INVENTOR(S) : Jean-Pierre Robin, Robert Kiss, Thierry Imbert Page 3 of 3

It is certified that error appears in the above-indentified patent and that said Letters Patent is hereby corrected as shown below:

Column 25, line 50: "epipodphyllotoxin" should read -- epipodophyllotoxin --.

Column 25, line 56: "epipodphyllotoxin" should read -- epipodophyllotoxin --.

Signed and Sealed this

Seventeenth Day of February, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,643,885
DATED : July 1, 1997
INVENTOR(S) : J. Pierre Robin, R. Kiss, T. Imbert It is certified that error appears in the above-identified patent and that said Letters Patent is hereby corrected as shown below:

Column 21, line 64: "claim 1" at the end of the line, should read -- claim 5 --.

Signed and Sealed this

Twenty-sixth Day of May, 1998

Attest:

BRUCE LEHMAN

*Attesting Officer*          *Commissioner of Patents and Trademarks*